US008057412B2

(12) United States Patent
Tsai

(10) Patent No.: US 8,057,412 B2
(45) Date of Patent: Nov. 15, 2011

(54) APPARATUS FOR ADJUSTING A SPINE

(76) Inventor: Richard Tsai, Darlington, PA (US)

( * ) Notice: Subject to any disclaimer, the term of this patent is extended or adjusted under 35 U.S.C. 154(b) by 1187 days.

(21) Appl. No.: 11/763,749

(22) Filed: Jun. 15, 2007

(65) Prior Publication Data

US 2008/0312690 A1 Dec. 18, 2008

(51) Int. Cl.
*A61F 7/00* (2006.01)

(52) U.S. Cl. ........................................ 601/135; 606/237

(58) Field of Classification Search .................... 601/72, 601/74, 80, 46, 48, 107, 125, 134, 135, 136, 601/137, 138; 128/845; 606/237, 240, 201, 606/204; 607/79; 15/110, 113, 224, 227, 15/425, 143.1, 244.1; D24/214; 401/7, 8
See application file for complete search history.

(56) References Cited

U.S. PATENT DOCUMENTS 871,121 A 11/1907 D'Humy
1,342,597 A 6/1920 Post
1,398,150 A 11/1921 Pollard
1,640,536 A * 8/1927 David ........................... 601/135
2,063,818 A 12/1936 Mankinen
2,180,775 A * 11/1939 Stevens ......................... 606/237
2,447,698 A * 8/1948 Haberer ......................... 606/240
2,818,854 A * 1/1958 Johnson ......................... 606/240
D223,690 S * 5/1972 Koizumi ....................... D24/214
3,901,222 A 8/1975 Muramatsu
4,230,099 A 10/1980 Richardson
4,705,030 A 11/1987 Tepperberg
4,785,801 A 11/1988 Speece
5,498,233 A * 3/1996 Stojanovic ...................... 602/19
6,036,719 A 3/2000 Meilus
6,305,040 B1 * 10/2001 Myler ............................... 5/636
6,312,396 B1 11/2001 Muller
6,942,631 B2 9/2005 Hepburn et al.
7,060,085 B2 6/2006 Graham et al.
7,087,004 B1 * 8/2006 Berke ........................... 482/136
7,097,626 B2 8/2006 Louis et al.
2003/0204153 A1 10/2003 Chen
2005/0251071 A1 11/2005 Zhadanov et al.
2007/0276438 A1 * 11/2007 Meglin et al. ................. 606/237
2008/0200853 A1 * 8/2008 Tielve ........................... 601/134
2010/0236560 A1 * 9/2010 Rambo et al. ................. 128/845

* cited by examiner

*Primary Examiner* — Quang D Thanh
(74) *Attorney, Agent, or Firm* — Tarolli, Sundheim, Covell & Tummino LLP

(57) ABSTRACT

An apparatus includes a frame having a substantially planar first portion and a substantially planar second portion. The first and second portions are spaced rigidly apart from each other in a substantially parallel orientation to define a passage that extends through the frame between the first portion and the second portion. The passage is dimensioned and configured to receive a hand. A central axis extends longitudinally through the passage. The apparatus further comprises a first pad and a second pad located on an exterior of the first portion of the frame and spaced apart from each other to provide a channel that extends longitudinally between the first pad and the second pad substantially orthogonal to the central axis. The channel may be configured to align with the spine where the first pad and the second pad are positioned to lie on opposing sides of the spine.

18 Claims, 4 Drawing Sheets

APPARATUS FOR ADJUSTING A SPINE

TECHNICAL FIELD

The present invention is directed to chiropractic instruments, and in particular, is directed to an apparatus for adjusting a spine.

BACKGROUND OF THE INVENTION

Various devices and aids have been developed to relieve back pain and the like. For example, many types of back braces, belts, etc., are presently or have been previously available. However, back pain and the like is often a result of misaligned vertebrae of the spine, which can result in pinched nerves and other related conditions. Such misalignment frequently requires treatment by a chiropractor. Due to the extent and variance in back problems requiring chiropractor manipulation, many times the chiropractor will have to perform dozens of manipulations in a given day and hundreds during a given week. Many of the manipulations are done with the chiropractor's hands alone. Consequently, the chiropractor's hand can be exposed to significant stress and strain from performing many types of manipulations. This can lead to cramping and/or arthritis in the chiropractor's hand and fingers. Thus, there is a need for a chiropractic device that both facilitates chiropractic manipulation and relieves unnecessary stress on the chiropractor's hands.

SUMMARY

In accordance with the present invention, an apparatus for adjusting a spine is provided.

One aspect of the invention provides an apparatus that includes a frame having a substantially planar first portion and a substantially planar second portion. The first and second portions are spaced rigidly apart from each other in a substantially parallel orientation to define a passage that extends through the frame between the first portion and the second portion. The passage is dimensioned and configured to receive a hand. A central axis extends longitudinally through the passage. The apparatus further comprises a first pad and a second pad located on an exterior of the first portion of the frame and spaced apart from each other to provide a channel that extends longitudinally between the first pad and the second pad substantially orthogonal to the central axis. The channel may be configured to align with the spine where the first pad and the second pad are positioned to lie on opposing sides of the spine.

In accordance with a further embodiment of the present invention, an apparatus for adjusting a spine is provided. The apparatus includes a rigid frame having a substantially planar first surface spaced apart from a substantially planar second surface by side portions. A passage configured to receive a hand extends through the frame between the first surface and the second surface. A central axis extends through the passage, and a notch is formed in the first surface of the frame and extends through part of the side portions of the frame. A first pad is disposed on the first surface on one side of the notch. A second pad is disposed on the first surface on another side of the notch in an opposing spaced apart relationship with the first pad to form a channel along the first surface of the frame that includes at least a substantial portion of the notch. The channel and the notch can be substantially orthogonal to the central axis.

Still another embodiment of the present invention provides an apparatus that includes a rigid frame. The frame includes a passage dimensioned and configured to receive a user's hand between rigidly spaced apart generally planar portions thereof. A central channel extends substantially linearly along a first of the generally planar portions the frame so as to define laterally spaced apart contact portions of the frame. The contact portions of the frame have adjacent edges that are spaced apart from each other by the central channel. At least one resilient pad is attached to the first of the generally planar portions of the frame, such as may extend over each of the contact portions of the frame.

BRIEF DESCRIPTION OF THE DRAWINGS

The foregoing and other features and advantages of the invention will become apparent to those skilled in the art to which the invention relates upon reading the following description with reference to the accompanying drawings, in which.

DETAILED DESCRIPTION

Figure 1:
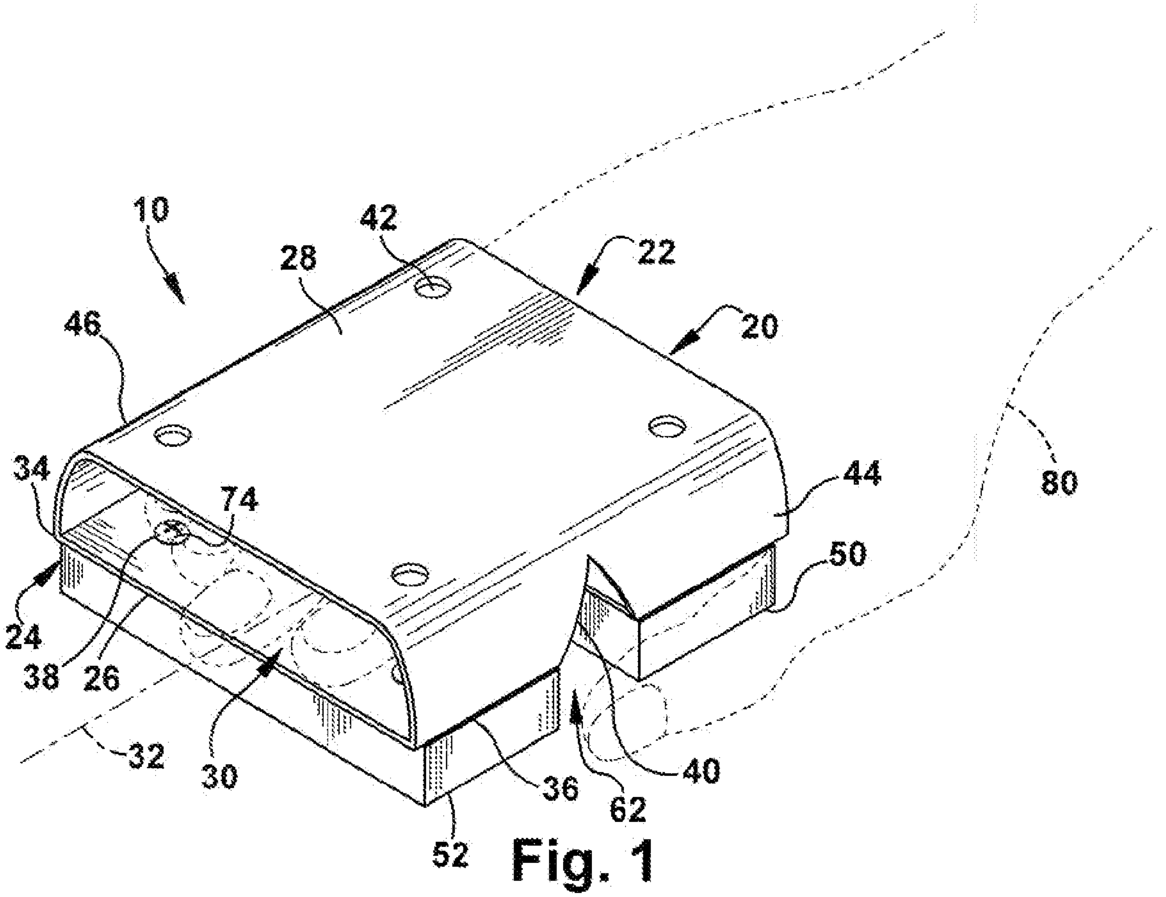
FIG. 1 is an isometric view of an apparatus in accordance with an embodiment of the invention.
Figure 2:
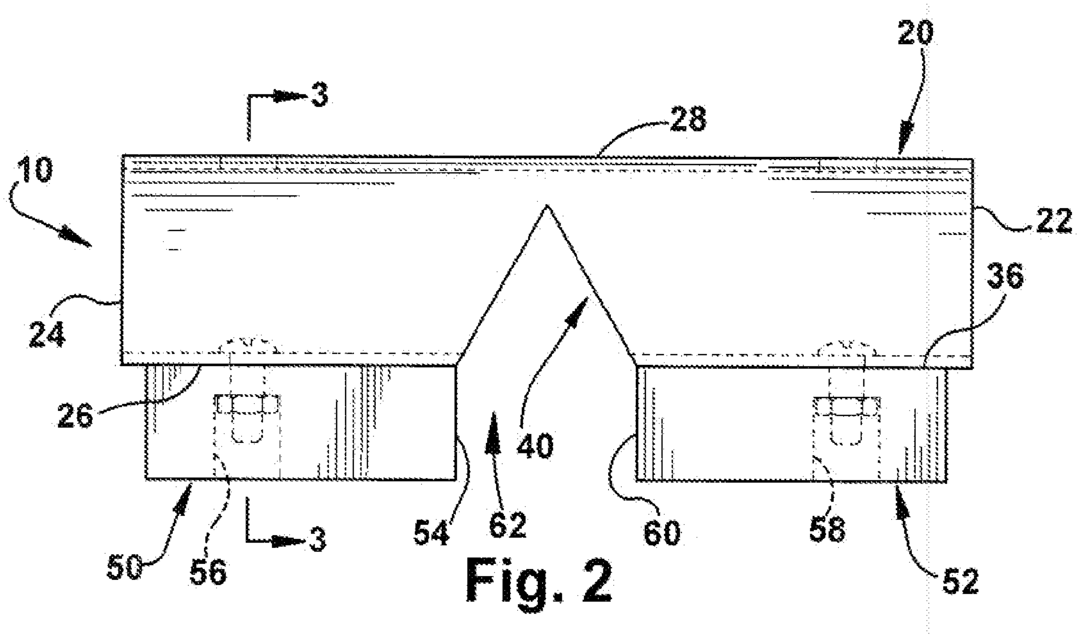
FIG. 2 is a front view of the apparatus of FIG. 1.

An apparatus 10 in accordance with the present invention is depicted in FIGS. 1-3. Thus, the various views of FIGS. 1-3 may be referred to for purposes of the following description in which like reference numbers refer to similar features in the various views.

The apparatus 10 includes a frame 20 having a generally rectangular profile, although other profiles, such as square, elliptical or the like, may be utilized. The frame 20 provides a substantially rigid and hollow support structure that extends between a proximal end 22 and a distal end 24. The frame 20 includes a first portion 26 and a second portion 28. The first portion 26 and second portion 28 can be substantially planar.

In the example of FIGS. 1-3B, the first portion 26 and second portion 28 are spaced rigidly apart from each other in a substantially parallel orientation by side portions 44 and 46 that extend between and interconnect the first and second portions. The spatial relationship of the first and second portions 26 and 28 and side portions 44 and 46 defines a passage 30 that extends through the frame 20. A central axis 32 extends longitudinally through the passage 30. The passage 30 is dimensioned and configured to receive a hand, indicated by dashed lines 80. The frame 20 and passage 30 thus can be considered means for receiving and for protecting a user's hand.

Since the size and shape of a user's hand can vary from person to person, it is understood that the size and shape of the passage 30 (and thus the size of the frame 20) can also vary from that shown. For example, the frame 20 can be provided in a plurality of different sizes to accommodate a range of typical sizes for user's hands. Alternatively, the frame 20 and passage 30 can be dimensioned and configured to a custom size and configuration for different users. While the passage 30 is depicted as being substantially rectangular, other shapes and contours could be provided.

The frame 20 can be made from a substantially rigid material, such as metal or plastic. As one example, the frame 20 can be formed from a thin sheet of stainless steel or a suitable alloy that has been bent into an appropriately dimensioned and configured rectangular frame. Alternatively or additionally, the frame can be fabricated as a single piece (e.g., a monolithic structure) according to other methods, such as by molding, extrusion or according to other known or yet-to-be developed fabrication techniques. Depending on how the frame 20 is fabricated, the frame 20 can provide a continuous structure (as shown in FIGS. 1-3) or the construction can result in one or more seams where ends of the structure abut.

As depicted in FIG. 1, the first portion 26 of the frame 20 may include a plurality of apertures 38 that extend entirely through such portion. The plurality of apertures 38 may be threaded and configured to receive threaded fasteners. Alternatively the apertures 38 may be unthreaded, although still configured to receive threaded fasteners. The second portion 28 of the frame 20 may include apertures 42 that are aligned with the apertures 38 in the first portion 26 so as to provide access to the first portion 26 through the passage 30. The apertures 42 may be slightly larger than the apertures 38 to facilitate construction and repair of the apparatus 10, such as described herein. For instance, the apertures 42 are sized to accommodate a standard screwdriver, as will be hereinafter described. Although FIG. 1 depicts four apertures in the first portion 26 and second portion 28, it will be appreciated that any number of apertures may be utilized.

The frame 20 further includes a first side edge 34 and a second side edge 36 spaced apart from each other by the first and second portions 26 and 28 of the frame. The side edges 34 and 36 also extend from the proximal end 22 to the distal end 24 of the frame 20.

The apparatus 10 further includes a first pad 50 and a second pad 52 secured to the exterior of the first portion 26 of the frame 20. The first pad 50 and second pad 52 can be made of a flexible, yet resilient material. This may include synthetic or natural rubber, a polymer material, or a foam cell matrix, for example. The pads 50 and 52 can be formed of a single unitary material or the pads may include multiple layers that might have different material properties. For example, a given pad 50, 52 might include a slightly softer, flexible material mounted on more rigid substrate. Those skilled in the art will understand and appreciate other types of pads and materials that can be utilized to form pads appropriate for use in the apparatus 10.

The pads 50 and 52 are spaced apart from each other to provide a channel 62 that extends longitudinally between the first pad 50 and the second pad 52 and aligned substantially orthogonal to the central axis 32. The channel 62 is dimensioned and configured to align with the spine of a patient where the first pad 50 and second pad 52 are positioned to reside on opposing sides of the spine.

The apparatus can also include a notch 40 that extends from the first edge 34 to the second edge 36 substantially along the midline of the frame 20. The notch 40 also extends substantially orthogonal to the central axis 32 and further may form part of the channel. In the example of FIGS. 1 and 2, the notch 40 includes a substantially V-shaped cut that extends partially into the side portions 44, 46. The notch 40 also includes a substantially rectangular section removed (e.g., cut) from the first portion 26 of the frame 20 between the edges 34 and 36. Although the notch 40 is depicted as having a substantially V-shaped (or triangular) profile in FIGS. 1 and 2, those skilled in the art will appreciate that the notch 40 may include other cross-sectional shapes, such as square or hemispherical or the like. If the frame 20 includes notch 40, the notch 40 will be aligned with, and form part of, the channel 62. Thus, the notch 40 provides a deeper channel between the pads 50 and 52 while still affording the frame with sufficient structural rigidity of the frame. The first pad 50 and second pad 52 may be attached to the first portion 26 on opposing sides of the notch 40 as shown in FIGS. 1 and 2.

The first pad 50 and second pad 52 can be provided with substantially the same length as the frame 20 between the side edges 34 and 36, such as shown in FIG. 1. Alternatively, the first pad 50 and second pad 52 may extend beyond the first edge 34 and/or second edge 36 of the frame 20 or be shorter than the distance between such edges. Each pad 50, 52 may be substantially rectangular in nature, although other shapes, such as triangular or hemispherical are contemplated. Regardless of the shape, the first pad 50 and second pad 52 each have an edge 54 and 60, respectively, that can be positioned adjacent to the notch 40. The adjacent edges 54 and 60, for example can be linear (or straight edges) that extend substantially parallel to the notch 40 to define the channel 62. FIG. 2 depicts that edge 54 on the first pad 50 and edge 60 on the second pad 52 extend substantially parallel to notch 40 from the first edge 36 to the second edge 36 of the frame 20. While the example of FIG. 2 depicts the side edges 54 and 60 as defining substantially parallel planar surfaces, such surfaces might alternatively be angled, such as tapering from the distal (or contact) surface of the pad to the opposing surface of the pad that engages the frame 20. These edges 54, 60 further can be used to facilitate aligning the apparatus 10 with the spine of the patient.

Figure 3A:
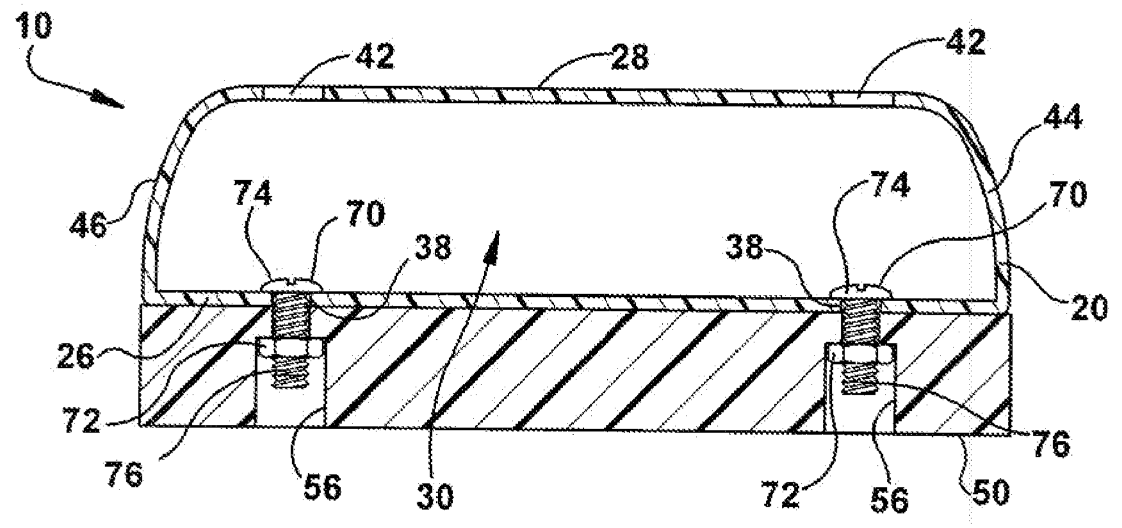
FIG. 3A is a section view of the apparatus of FIG. 2 taken along line 3-3.
Figure 3B:
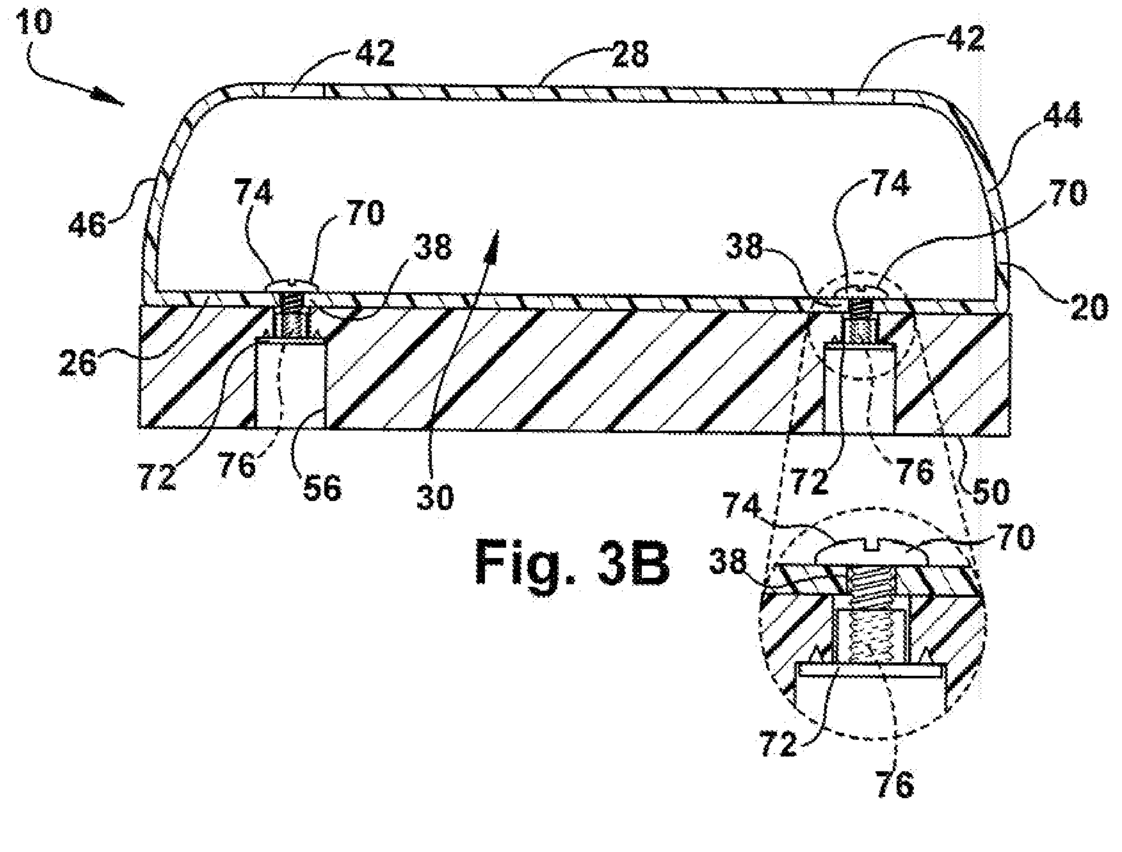
FIG. 3B is a section view of the apparatus of FIG. 2 taken along line 3-3 illustrating an alternative fastening means.

As mentioned above, the first and second pads 50 and 52 can be attached or secured to the frame by various fastening means. As one example, the first pad 50 and second pad 52 may include passages 56 and 58, respectively, arranged to align with the apertures 38 in the first portion 26 of the frame 20. Passages 56 in the first pad 50 and passages 58 in the second pad 52 extend entirely through the first pad 50 and second pad 52, respectively to permit passage of a threaded fastener into such passage. The passages 56 and 58 can further include a portion having a larger diameter so as to define a shoulder portion configured to receive securing means, such as a threaded nut (FIG. 3A) or a pronged t-nut 72 (FIG. 3B). For example, in FIG. 3A, the nuts 72 thus may engage the shoulder portion of the respective passages so as to, in response to threading the fasteners onto such nuts, urge the respective pads into a fixed engagement with the frame 20. In the example of FIG. 3B, where pronged t-nuts 72 are used, threading of the fasteners onto such t-nuts urges the prongs into engagement with the shoulder portion of the passage, which prevents the nut 72 from rotating relative to the passage. This further ensures that the threaded connection between the fasteners and the nuts 72 is fixed.

As discussed above, the apertures 42 in the second portion 28 can be designed to accommodate a screwdriver and fastener 70. For example, apertures 42 are designed to accommodate passing both a shank portion 76 and a head portion 74 of the fastener 70 through such apertures. In contrast, apertures 38 can be designed to accommodate the shank portion 76 but not the head portion 74 of the fastener 70 (FIGS. 3A-3B). Thus, the first pad 50 and second pad 52 may be secured to the frame 20 by at least one fastener 70, such as a threaded fastener. Alternatively, each pad 50, 52 could be secured to the frame 20 by other fastening means, such as adhesive, compression fitting, rivets, Velcro®, or the like.

By way of further example, to secure the first pad 50 to the first portion 26 of the frame 20, the first pad 50 is placed against the exterior surface of the first portion 26 as shown in FIG. 2. The fastener 70 may then be placed in the passage 30 and then inserted, or threaded, into the aperture 38 in the first portion 26 of the frame 20 such that the shank portion 76 of the fastener 70 enters the passage 56 in the first pad 50, while the head portion 74 of the fastener 70 remains within the passage 30 due to the size of the aperture 38 relative to the fastener 70. Alternatively, the fastener 70 may be inserted through aperture 42 in the second portion 28, the passage 30, and finally into aperture 38 in the first portion 26. In either case, a corresponding nut 72 can then be inserted through the opposite side of same passage 56 in the first pad 50 to engage the shank portion 76 of the fastener 70. A screwdriver can then be inserted through the aperture 42 in the second portion 28 and the passage 30 to access the head portion 74 of the fastener 70 (not shown). The fastener 70 can then be tightened with the nut 72 to secure a portion of the first pad 50 to the frame 20 (FIG. 3A-3B). The length of the fastener 70 may be such that the shank portion 76 of the fastener 70 does not extend entirely through the nut 72 (FIG. 3B). This ensures that the shank portion 76 of the fastener 70 does not come into contact with the patient during use of the apparatus 10, which might otherwise cause discomfort to the patient. The process can be repeated for each fastener 70 in the first pad 50 until the first pad 50 is completely secured to the first portion 26 of the frame 20.

Similarly, a fastener 70 may be placed in the passage 30 and then inserted, or threaded, into the aperture 38 in the first portion 26 of the frame 20 such that the shank portion 76 of the fastener 70 enters the passage 58 in the second pad 52, while the head portion 74 of the fastener 70 remains within the passage 30 due to the size of the aperture 38 relative to the fastener 70. A corresponding nut 72 can then be inserted through the opposite side of same passage 58 in the second pad 52 to engage the fastener 70. A screwdriver can then be inserted through the aperture 42 in the second portion 28 and the passage 30 to access the head portion 74 of the fastener 70. The fastener 70 can then be tightened with the nut 72 to secure a portion of the second pad 52 to the frame 20. The process is again repeated for each fastener 70 in the second pad 52 until the second pad 52 is adequately secured to the first portion 26 of the frame 20.

Although it has been shown that each fastener 70 is inserted through passage 30 and aperture 38 and threadably engaged with nut 72 inserted through passages 56 or 58 to secure the first pad 50 or the second pad 52, respectively, to the frame 20, it will be appreciated by those in the art that apertures 38 and passages 56 and 58 may be configured to allow each fastener 70 to be inserted through passage 56 or 58 and each nut 72 to be inserted through passage 30 to secure pads 50 and 52 to the frame 20.

The ability to access the head portion 74 of each fastener 70 by utilizing the apertures 42 in the second portion 28 and the apertures 38 in the first portion 42 facilitates the replacement of the first pad 50 and the second pad 52 after prolonged use or damage. Replacement of the first pad 50 and the second pad 52 may be accomplished by performing the above-mentioned steps for securing the first pad 50 and the second pad 52 to the frame 20 in reverse. A screwdriver can be inserted through the aperture 42 in the second portion 28 and the passage 30 to access the head portion 74 of each fastener 70. The fastener 70 can then be loosened from the nut 72 to loosen a portion of the first pad 50 or second pad 52 from the frame 20. The process is again repeated for each fastener 70 in first pad 50 or the second pad 52 until the first pad 50 or second pad 52 is released from the first portion 26 of the frame 20.

Figure 4:
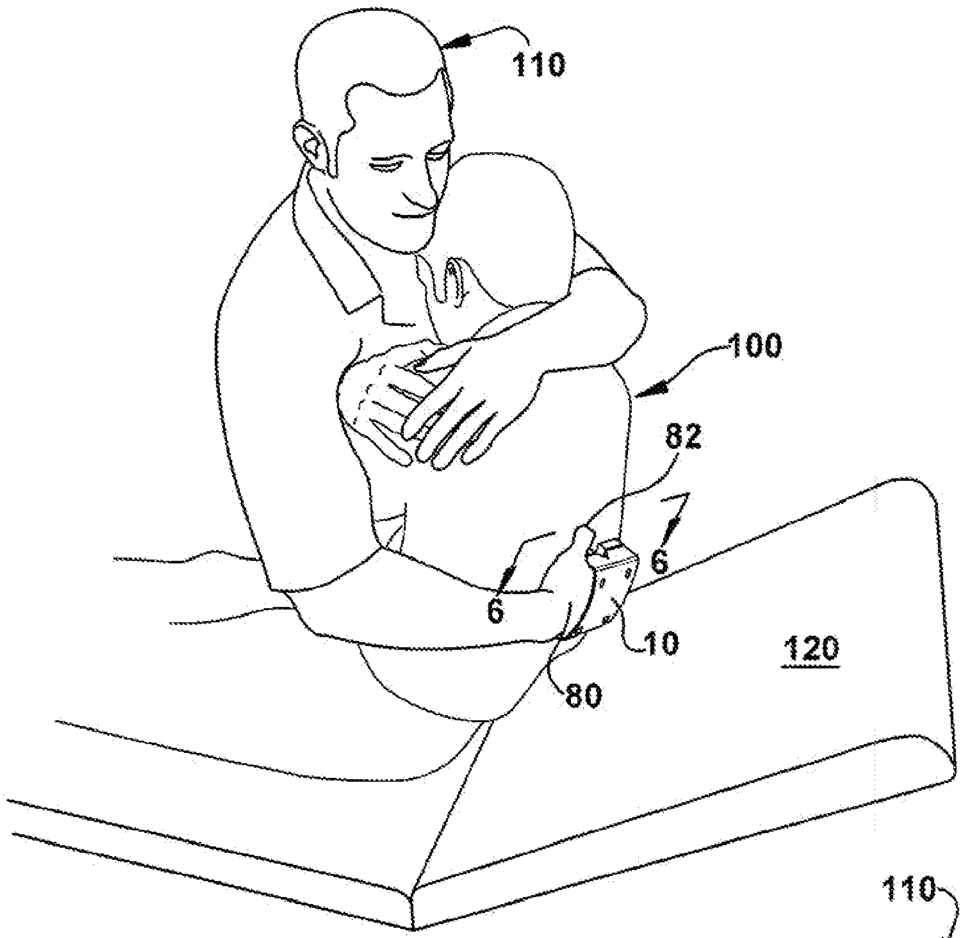
FIG. 4 is a schematic illustration of an apparatus being used by a practitioner in accordance with an embodiment of the invention.
Figure 5:
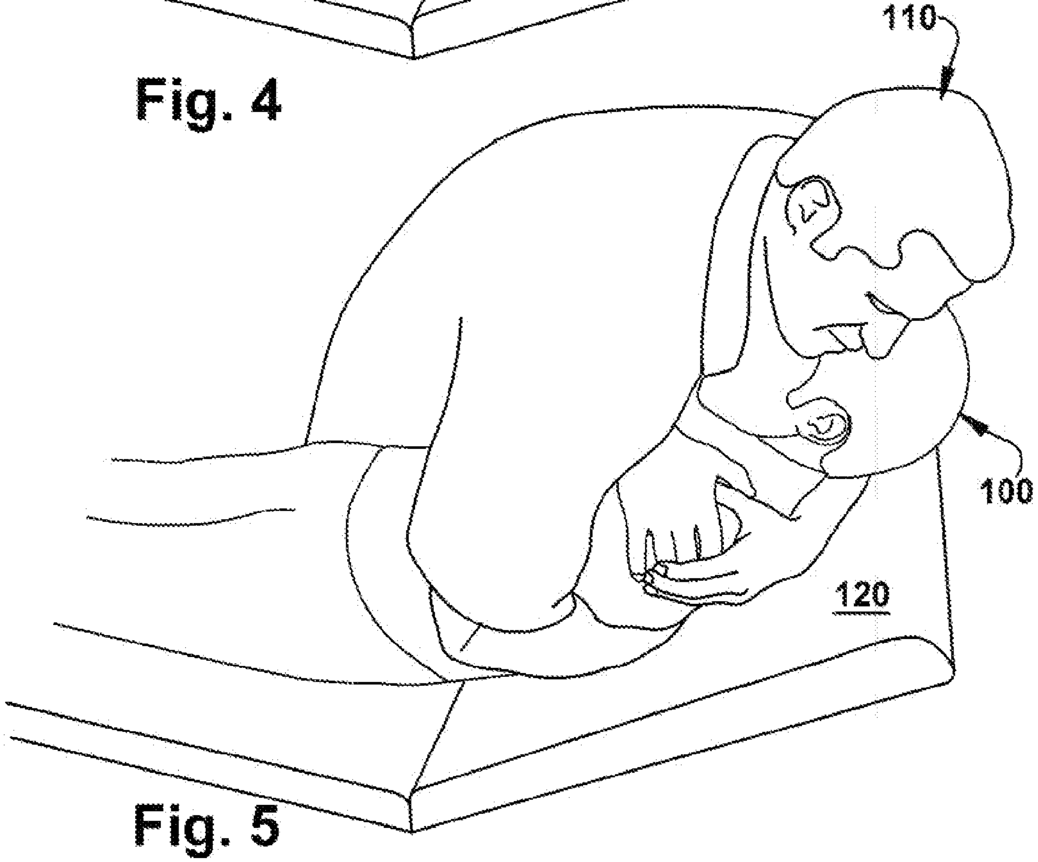
FIG. 5 is a schematic illustration of the practitioner performing a chiropractic manipulation using the apparatus in accordance with an embodiment of the invention.
Figure 6:
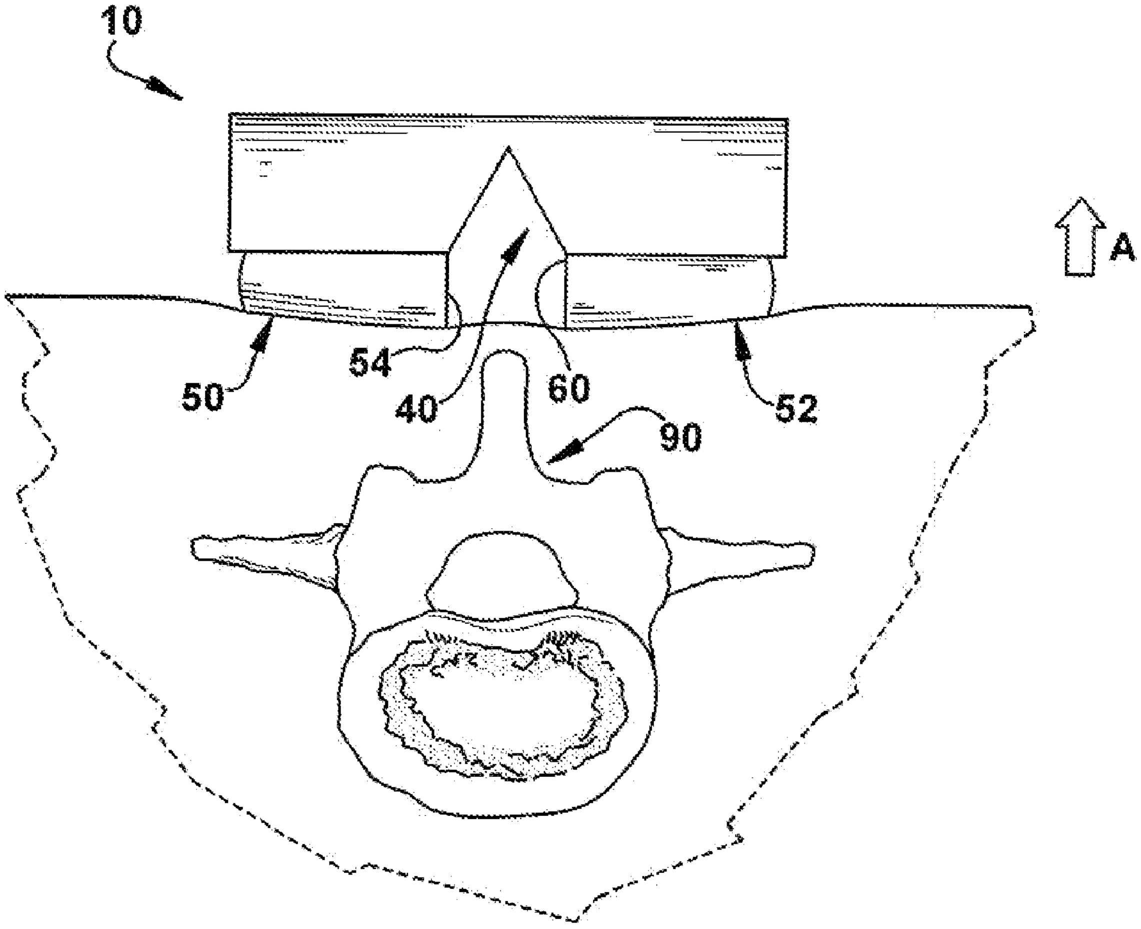
FIG. 6 is a partial section view of FIG. 4 taken along line 6-6 illustrating a relative alignment of the apparatus with a patient's spine.

An example use of the apparatus 10 for performing chiropractic adjustment (e.g., the anterior adjustment) will be better appreciated with reference to FIGS. 4, 5 and 6. To utilize the apparatus 10, the chiropractor 110 inserts a hand 80 into the proximal end of the frame 20 such that the palm of hand 80 resides within the passage 30. A portion of the user's fingers may extend through the distal end of the frame 20 from the proximal end 22 to the distal end 24 as shown by the phantom lines in FIG. 1. In this orientation, the hand 80 extends substantially transverse to the first pad 50, the second pad 52, the channel 62, and the notch 40 in the frame 20 (if applicable). The thumb 82 remains outside of the apparatus 10, and will be used to tactilely locate the spine 90 of the patient 100.

In use, the patient 100 is seated generally facing the practitioner 110 with arms crossed in an 'X' fashion across his/her chest as shown in FIG. 4. The practitioner 110 holds the patient 100 against him, such as chest-to-chest by placing one arm around the patient's back and pulling the patient 100 towards him, bending him at the waist. With the apparatus 10 on the user's other hand 80, the practitioner 110 reaches his other arm around the patient 100 and places the apparatus 10 near the patient's spine. Additionally and advantageously, the practitioner 110 can use his free thumb 82 to tactilely locate the position of the patient's spine 90 at a location where chiropractic manipulation is to be performed. Although the right hand 80 is depicted in FIG. 4, the left hand could likewise be used, depending on the chiropractic manipulation performed and/or the dexterity of the practitioner 110. Once the practitioner 110 locates the desired portion of the patient's spine 90 for manipulation, the apparatus 10 is placed into engagement with the patient's back at the position to be manipulated. For instance, the first pad 50 and second pad 52 on the apparatus 10 can be positioned substantially parallel to and on opposite sides of the patient's spine 90 at the manipulation site and the channel 62 and/or the notch 40 is aligned over the spine 90 (FIG. 6).

To perform the anterior adjustment, for example, the practitioner 110 continuously holds the patient 100 against him and gradually he leans the patient 100 back until the exterior surface of the second portion 28 of the frame 20 engages the table 120 on which the patient is lying (i.e., the apparatus 10 is sandwiched between the table and the patient 100), such as shown in FIG. 5. The anterior adjustment could likewise be performed by the chiropractor 110 placing his left hand on the patient's chest and leaning the patient 100 back instead of the chiropractor 110 holding the patient 100 against him in a hugging fashion. In either case, the patient 100 will then be substantially parallel to the table 120. In this position, the first pad 50 and second pad 52 will provide some cushioning between the frame 20 and the patient's spine 90 as the weight of the patient 100 is applied to the apparatus 10 in the direction indicated by 'A' (FIG. 6). The weight of the patient 100 is transferred from the first pad 50 and second pad 52 into the frame 20.

The practitioner can also apply additional force for performing the chiropractic manipulation. This may be accomplished, for example, by the chiropractor removing his hand 80 from the passage 30 in the frame 20 while the apparatus 10 remains sandwiched between the table 120 and the patient 100. The chiropractor 110 can then use both hands to apply force to the patient's chest. Such a procedure may be required, for example, when the patient's torso is too large for the chiropractor 110 to wrap both arms around, or to ensure proper chiropractic manipulation where the patient's spine 90 is more resistant to adjustment.

Due to the rigid nature of the frame 20, the chiropractic manipulation is accomplished without placing undue stress on the hand 80 of the practitioner 110. The apparatus 10, and not the chiropractor's hand 80, performs the chiropractic manipulation while the hand 80 remains unstressed (e.g., protected) within the frame 20 during the procedure. The apparatus 10 thus allows the practitioner 110 to perform many chiropractic manipulations while mitigating discomfort or damage to the practitioner's hand 80 that can otherwise occur in the absence of the apparatus.

The apparatus 10 generally has a larger surface area than the chiropractor's hand 80 such that chiropractic adjustment performed with the apparatus 10 tends to be more comfortable to the patient 100 than when the chiropractor 110 uses his hands alone. The efficacy of the chiropractic manipulation may thus be increased by allowing the chiropractor 110 to apply more force during each adjustment without applying stress to his hand 80 or generating patient 100 discomfort.

From the above description of the invention, those skilled in the art will perceive improvements, changes and modifications. Such improvements, changes and modifications within the skill of the art are intended to be covered by this application and the appended claims.

Having the described the invention, the following is claimed:

1. An apparatus for adjusting a spine comprising:

a frame including a substantially planar first portion and a substantially planar second portion spaced rigidly apart from each other in a substantially parallel orientation, a passage extends through the frame between the first portion and the second portion thereof, the passage being dimensioned and configured to receive a hand, wherein a central axis extends longitudinally through the passage; and a first pad and a second pad located on an exterior of the first portion of the frame and spaced apart from each other to provide a channel that extends longitudinally between the first pad and the second pad substantially orthogonal to the central axis, whereby the channel is configured to align with the spine where the first pad and the second pad lie on opposing sides of the spine.

2. The apparatus of claim 1 wherein the first pad and the second pad comprise a sheet of a flexible and resilient material.

3. The apparatus of claim 2, wherein the flexible and resilient material further comprises at least one of a rubber material, a polymer material, and a foam cell material.

4. The apparatus of claim 1, wherein the frame comprises a rigid metal material.

5. The apparatus of claim 1, further comprising at least one fastener that secures each of the first pad and the second pad to the first portion of the frame.

6. The apparatus of claim 5, wherein the at least one fastener further comprises a plurality of threaded fasteners, the first portion of the frame comprising first apertures configured to receive the threaded fasteners for securing each of the first pad and the second pad to the first portion of the frame.

7. The apparatus of claim 6, wherein the second portion of the frame further comprises a plurality of spaced apart second apertures aligned with the first apertures of the first portion of the frame as to provide access to the first portion of the frame through the passage.

8. The apparatus of claim 1, wherein adjacent edges of the first pad and the second pad extend substantially parallel to the channel.

9. The apparatus of claim 1, wherein the first portion of the frame further comprises a notch that extends therethrough between spaced apart edges of the frame, the notch being aligned with and forming part of the channel.

10. The apparatus of claim 9, wherein the first portion and the second portion of the frame are spaced rigidly apart from each other by spaced apart side portions of the frame, the notch further comprising a substantially V-shaped cut that extends partially into the side portions of the frame and a substantially rectangular section cut from the first portion of the frame.

11. An apparatus for adjusting a spine comprising:

a substantially rigid frame having a substantially planar first surface spaced apart from a substantially planar second surface by side portions, a passage configured to receive a hand extends through the frame between the first surface and the second surface, a central axis extending through the passage, a notch is formed in the first surface of the frame and extends through part of the side portions of the frame;

a first pad disposed on the first surface on one side of the notch; and a second pad disposed on the first surface on another side of the notch in an opposing spaced apart relationship with the first pad to form a channel along the first surface of the frame that includes at least a substantial portion of the notch, the channel and the notch being substantially orthogonal to the central axis.

12. The apparatus of claim 11 wherein the first pad and the second pad comprise a sheet of a flexible and resilient material.

13. The apparatus of claim 11, wherein the frame comprises a rigid metal material.

14. The apparatus of claim 11, further comprising at least one fastener that secures each of the first pad and the second pad to the first surface of the frame.

15. The apparatus of claim 14, wherein the at least one fastener further comprises a plurality of threaded fasteners, apertures extending through at least the first surface of the frame to receive the threaded fasteners for securing each of the first pad and the second pad to the frame.

16. The apparatus of claim 11, wherein adjacent edges of the first pad and the second pad extend substantially parallel to the notch.

17. The apparatus of claim 16, wherein the notch extends between spaced apart edges of the frame, the notch being aligned with and forming part of the channel.

18. The apparatus of claim 11, wherein the first surface and the second surface of the frame are spaced rigidly apart from each other by spaced apart side portions of the frame, the notch further comprising a substantially V-shaped cut that extends partially into the side portions of the frame and a substantially rectangular section cut through the first surface of the frame.

* * * * *